(12) United States Patent
Stephens et al.

(10) Patent No.: US 10,751,497 B2
(45) Date of Patent: Aug. 25, 2020

(54) FACE MASK WITH SLEEVE AND FLAP

(71) Applicant: KONINKLIJKE PHILIPS N.V., Eindhoven (NL)

(72) Inventors: Nathaniel Stephens, Pittsburgh, PA (US); Duon Alex Truong, Plum Borough, PA (US); Dina Colangelo, Murrysville, PA (US); Lauren Patricia Chodkowski, Pittsburgh, PA (US); Jonathan Sayer Grashow, Cheswick, PA (US)

(73) Assignee: Koninklijke Philips N.V., Eindhoven (NL)

( * ) Notice: Subject to any disclaimer, the term of this patent is extended or adjusted under 35 U.S.C. 154(b) by 433 days.

(21) Appl. No.: 15/538,224

(22) PCT Filed: Dec. 15, 2015

(86) PCT No.: PCT/IB2015/059609
§ 371 (c)(1),
(2) Date: Jun. 21, 2017

(87) PCT Pub. No.: WO2016/103107
PCT Pub. Date: Jun. 30, 2016

(65) Prior Publication Data
US 2018/0001044 A1 Jan. 4, 2018

Related U.S. Application Data

(60) Provisional application No. 62/096,581, filed on Dec. 24, 2014.

(51) Int. Cl.
*A61M 16/06* (2006.01)
*A61M 16/00* (2006.01)

(52) U.S. Cl.
CPC .... *A61M 16/0627* (2014.02); *A61M 16/0063* (2014.02); *A61M 16/0605* (2014.02);
(Continued)

(58) Field of Classification Search
CPC ..... A41G 7/00; A61M 16/0057; A61M 16/06; A61M 16/0611; A61M 16/0616;
(Continued)

(56) References Cited

U.S. PATENT DOCUMENTS

2003/0196658 A1* 10/2003 Ging ..................... A61M 16/06
128/201.22
2003/0196659 A1* 10/2003 Gradon ............... A61M 16/065
128/201.26
(Continued)

FOREIGN PATENT DOCUMENTS

WO WO2013066195 A1 5/2013
WO WO2014141029 A1 9/2014

*Primary Examiner* — Annette Dixon
(74) *Attorney, Agent, or Firm* — Michael W. Haas

(57) ABSTRACT

A minimal weight patient interface device that delivers breathing gas to a user includes a cushion assembling including a support cushion assembly and a sealing member is described herein. In one exemplary embodiment, the support cushion assembly includes a wedge that is made of a high density foam received within a wedge receiving portion of the support cushion assembly. In the exemplary embodiment, the cushion assembly is formed by the sealing member fitting over the support cushion assembly. The sealing member, in one embodiment, is made of silicone, for example, having a low durometer value (e.g., between 5-10 Shore 00). Furthermore, in one embodiment, the patient interface device also includes a faceplate that is placed over the cushion assembly and is made of a thermoform, such as a high density foam laminated between two pieces of fabric, such as polyester.

15 Claims, 15 Drawing Sheets

(52) U.S. Cl.
CPC .... *A61M 16/0622* (2014.02); *A61M 16/0644*
(2014.02); *A61M 16/0683* (2013.01); *A61M
2202/0208* (2013.01); *A61M 2210/0606*
(2013.01)

(58) Field of Classification Search
CPC .......... A61M 16/0622; A61M 16/0633; A61M
16/0638; A61M 16/0644; A61M 16/0666;
A61M 16/0683; A61M 16/08; A61M
16/0816; A61M 16/0825; A61M 16/0875;
A61M 2016/0661; A61M 2205/42; A61M
2205/52; A61M 2210/0618; B29C
2043/3623; B29C 33/302; Y10S 264/30
See application file for complete search history.

(56) References Cited

U.S. PATENT DOCUMENTS

| | | | | |
|---|---|---|---|---|
| 2007/0125385 A1* | 6/2007 | Ho | ........................ | A61M 16/06 128/206.26 |
| 2008/0041388 A1* | 2/2008 | McAuley | .............. | A61M 16/06 128/206.24 |
| 2011/0186051 A1* | 8/2011 | McAuley | .............. | A61M 16/06 128/206.24 |
| 2012/0067349 A1* | 3/2012 | Barlow | ................. | A61M 16/06 128/205.25 |
| 2013/0014760 A1* | 1/2013 | Matula, Jr. | ............ | A61M 16/06 128/205.25 |

* cited by examiner

FACE MASK WITH SLEEVE AND FLAP

CROSS-REFERENCE TO RELATED APPLICATIONS

This patent application claims the priority benefit under 35 U.S.C. § 371 of international patent application no. PCT/IB2015/059609, filed Dec. 15, 2015, which claims the priority benefit under 35 U.S.C. § 119(e) of U.S. Provisional Application No. 62/096,581 filed on Dec. 24, 2014, the contents of which are herein incorporated by reference.

BACKGROUND OF THE INVENTION

1. Field of the Invention

The present invention generally relates to a patient interface device having minimal weight, and, in particular, to a minimal weight face mask including a faceplate, a low durometer sealing member and flap, and a support cushion assembly including a wedge.

2. Description of the Related Art

It is generally known to deliver positive airway pressure ("PAP") therapy to treat various medical conditions, such as sleep apnea. Such known PAP therapies include continuous positive airway pressure ("CPAP") devices, which use constant positive pressure to maintain an airway of a patient receiving the therapy open. Other known PAP therapies also include variable airway pressure, which has the pressure provided to the patient's airway varied with the patient's respiratory cycle.

The various PAP therapies typically include a mask, a pressure generating device, and a conduit to deliver breathing gas from the pressure generating device to the patient through the mask. Typically, these masks are formed out of a cushion material that directly contacts the patient's face. However, these materials are often uncomfortable for the patient while they wear the mask for long durations of time (e.g., overnight while sleeping). For example, if the cushion is too heavy, the weight of the cushion on the patient's face will make the mask wearing experience particularly difficult and unpleasant. In some situations, patients may remove the mask due to the uncomfortableness felt, and therefore they will not receive the needed therapy.

Typical face masks include one or more headgear straps that secure the mask to the patient's face. Normally the headgear straps require a large amount of tension to be secured to the patient's face. The pressure on the patient's face due to the tension applied by the straps to the mask can become extremely uncomfortable for the user. Furthermore, as the masks are often substantially rigid (e.g., a rigid faceplate or cushion), pressure points along the patient's face where the mask interfaces with the patient's face are created. These pressure points will hinder an adequate seal from forming, which in turn, decreases the effect of the therapy being delivered. This problem is further exacerbated by overly tight headgear straps, which will also generate pressure points leading to poor seals.

Other issues that commonly arise from most masks relate to the mask's faceplate. The faceplate should be substantially rigid in order to provide general support for the mask and to the patient so that the mask is retained on the patient's face throughout the administration of the therapy. Furthermore, the faceplate should be rigid enough to accept a conduit so that the breathing gas may be received by the patient. However, if the faceplate is too rigid, the facemask will not form an adequate seal with the patient's face. Additionally, headgear straps attached to the faceplate often times result in irregular pressure points along the patient's face, decreasing the quality of the seal between the mask and the patient's face. Furthermore, the overall weight of the mask is increased by having a rigid faceplate, as the material(s) commonly used for rigid faceplates cause the faceplate, and thus the mask itself, to become heavy, and therefor uncomfortable for the patient.

SUMMARY OF THE INVENTION

Accordingly, it is an objective of this invention to provide a lightweight face mask that provides an improved seal over conventional masks while also being more comfortable for a user to wear for long periods of time. This objective is achieved according to the present invention, in one exemplary embodiment, by providing a lightweight mask including a fabric faceplate, a low durometer silicon sealing member and flap, and a foam support cushion assembly.

In one exemplary embodiment, a minimal weight patient interface device operable to deliver breathing gas to a user is provided. The patient interface device includes a cushion assembly including a support cushion assembly and a sealing member. The support cushion assembly defines a first orifice and has at least one wall defining an inner surface of the support cushion assembly. The sealing member is disposed in the first orifice and covers the inner surface defined by the at least one wall. The sealing member defines a patient receiving orifice for receiving a portion of a face of the user responsive to the patient interface device being donned by the user, and the sealing member provides a sealing surface for creating a seal against the face of the user responsive to the patient interface device being donned by the user and prevents the support cushion assembly from contacting the face of the user. The support cushion assembly, in one embodiment, is made of a second material, such as foam. Furthermore, in the exemplary embodiment, the sealing member is made of silicon and has a substantially low durometer (e.g., 5-10 Shore 00).

In another exemplary embodiment, the patient interface also includes a faceplate. The faceplate includes a back portion that is placed over the front faceplate portion such that the faceplate abuts the sealing member and at least a portion of the cushion assembly. In the exemplary embodiment, the faceplate is made of a thermoform material, which, for example, is made of a piece of foam laminated between two pieces of fabric.

In yet another exemplary embodiment, the support cushion assembly also includes a wedge made of foam. The foam of the wedge, support cushion assembly, and thermoform, in a particular embodiment, are all different foams having different densities. For example, the foam included within the thermoform may be denser than the foam of the wedge, which may also be denser than the foam the support cushion assembly is made of. In the exemplary embodiment, the support cushion assembly also includes a wedge receiving portion operable to receive the wedge.

DETAILED DESCRIPTION OF EXEMPLARY EMBODIMENTS

Figure 1:
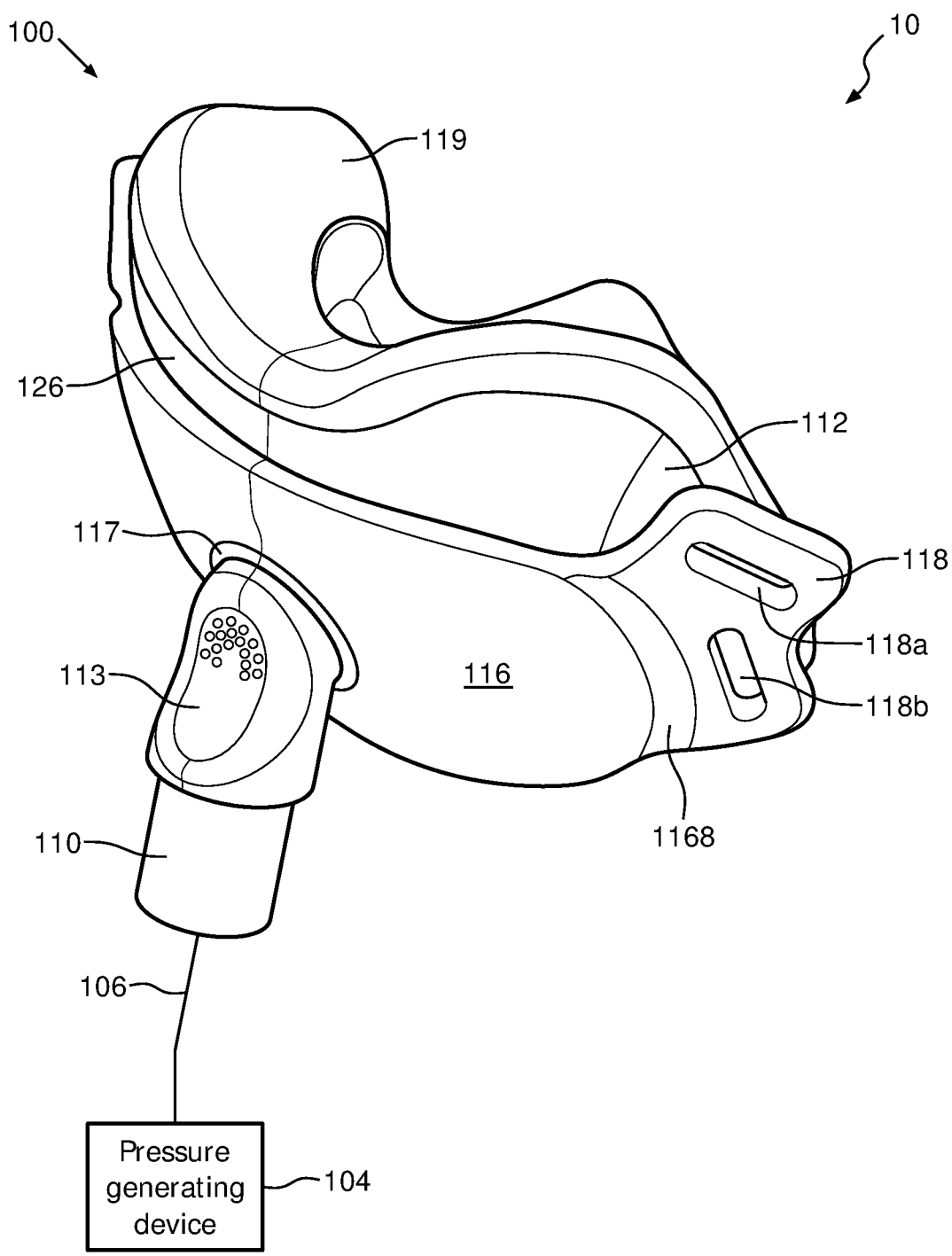
FIG. 1 is an isometric view of a patient interface device in accordance with various embodiments.

The present invention may take form in various components and arrangements of components, and in various techniques, methods, or procedures and arrangements of steps. The referenced drawings are only for the purpose of illustrated embodiments, and are not to be construed as limiting the present invention. Various inventive features are described below that can each be used independently of one another or in combination with other features. Furthermore, as used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" on another shall mean that the parts exert a force against one another either directly or through one or more intermediate parts or components. As employed herein, the term "number" shall mean one or an integer greater than one (e.g., a plurality). As used herein, a "substantially fluid tight seal" means that two surfaces sealingly engage each other in a manner that substantially limits passage of fluid or gas between the two surfaces (e.g., no more than 5% passage).

As used herein, the term "sealingly" or "sealed" in the context of an engagement, attachment or coupling means that two parts are coupled to one another with a substantially fluid tight seal. Direction phrases used herein including, but not limited to, top, bottom, right, left, upper, lower, front, back, rear, and derivatives thereof, relate to the orientation of the elements shown in the drawings and are not limiting upon the claims unless expressly recited therein.

Figure 2:
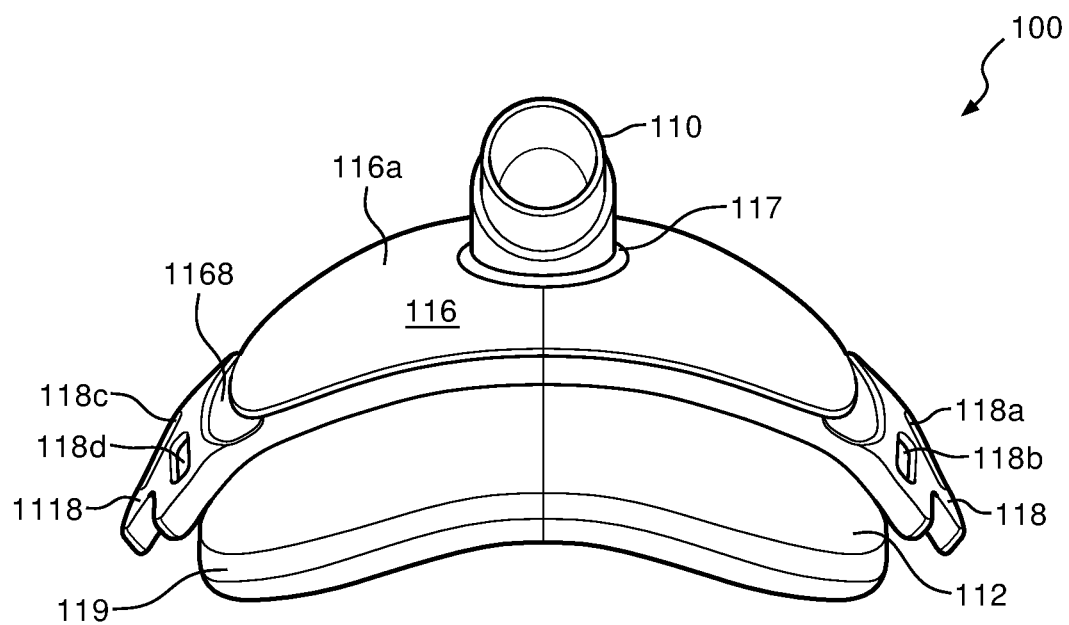
FIGS. 2-4 are bottom plane, top plane, top-cross sectional, and side plane views, respectively, of the patient interface device of FIG. 1 in accordance with various embodiments.
Figure 3A:
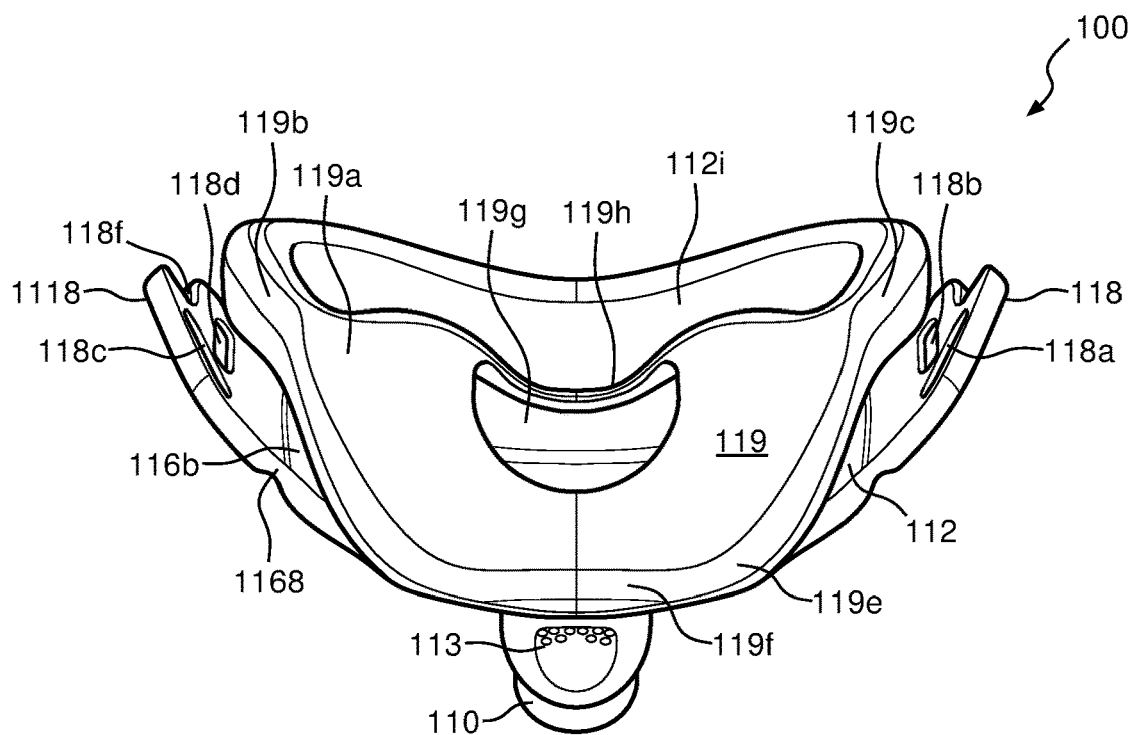
Figure 3B:
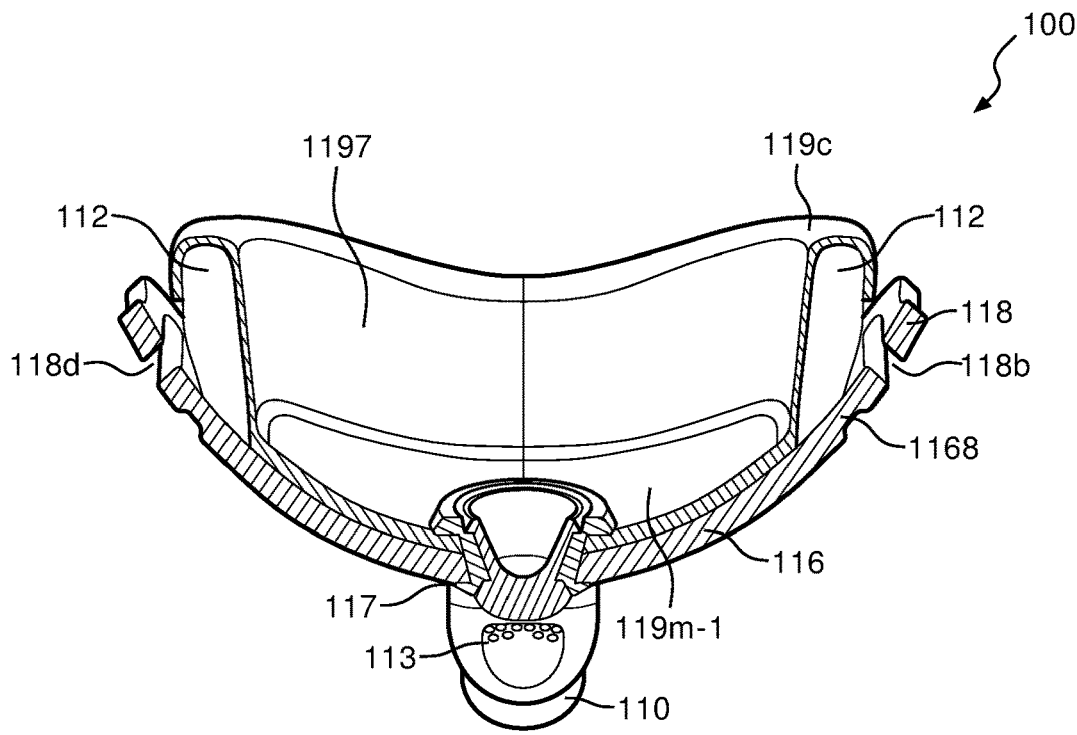
Figure 4:
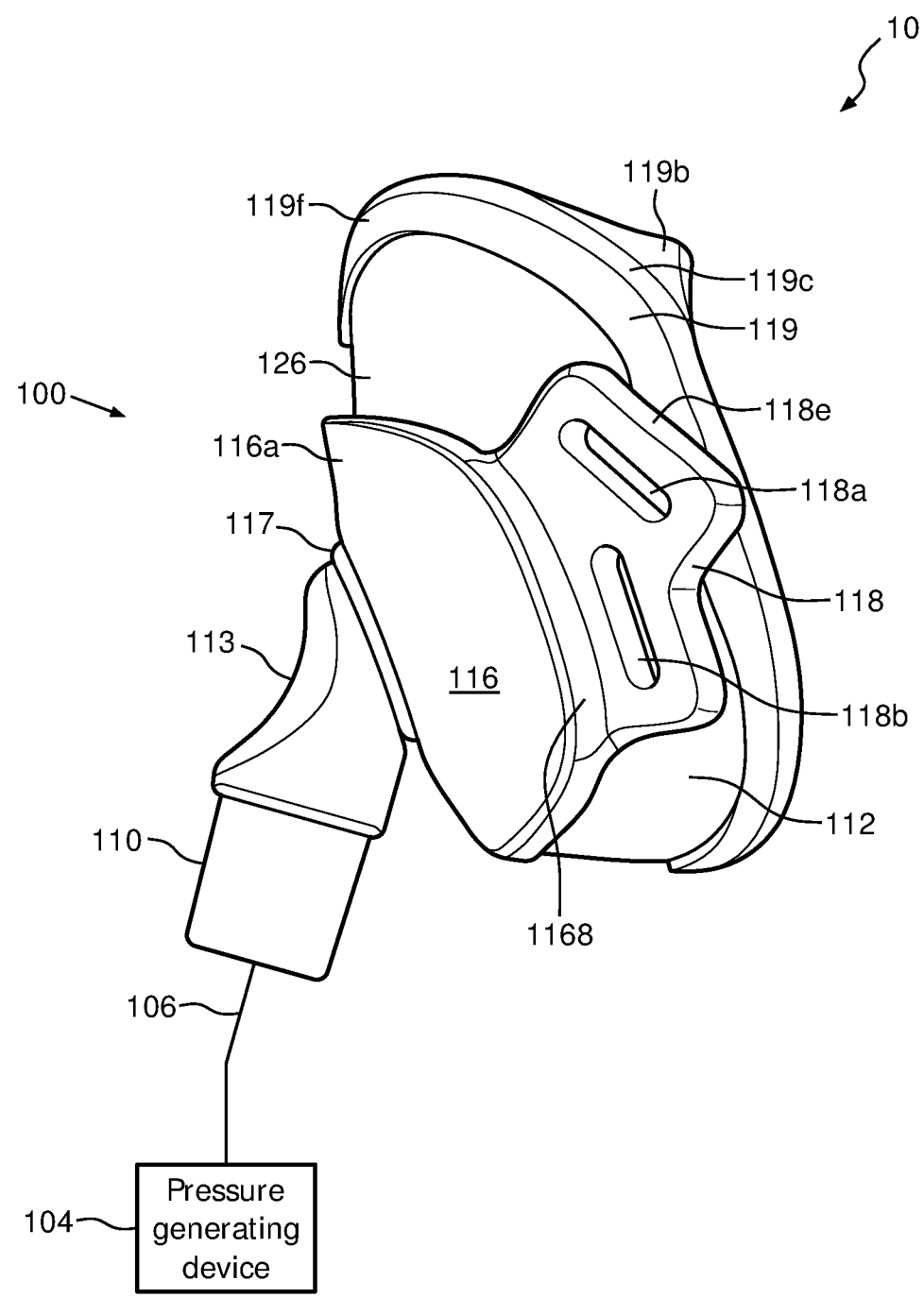

FIG. 1 is an isometric view of a patient interface device 100 of a system 10 in accordance with various embodiments. FIGS. 2-4 are bottom plane, top plane, top cross sectional, and side plane views, respectively, of patient interface device 100 of system 10 of FIG. 1 in accordance with various embodiments. A system 10, which is capable of providing a regimen of respiratory therapy to a patient according to one exemplary embodiment of the invention is generally shown in FIGS. 1 and 4, while FIGS. 2, 3A, and 3B generally show patient interface device 100 that interfaces with a patient. System 10 includes a patient interface device 100, a pressure generating device 104, and a delivery conduit 106. Patient interface device 100 includes an elbow conduit 110, which receives breathing gas from pressure generating device 104 via delivery conduit 106, which is coupled thereto. Pressure generating device 104 is structured to generate a flow of breathing gas and includes a variety of components including, but not limited to, ventilators, constant pressure support devices (such as a continuous positive airway pressure device, or CPAP device), variable pressure device (e.g., BiPAP®, Bi-Flex®, or C-Flex™ devices manufactured and distributed by Philips Respironics of Murrysville, Pa.), and/or auto-titration pressure support devices.

In the illustrated embodiment, patient interface device 100 includes a cushion assembly including a support cushion assembly 112, a low durometer sealing member and flap 119, and a faceplate 116 that allow breathing gas to be delivered to a patient's airway through both the patient's nose and mouth. It will be appreciated, however, that the illustrated embodiment is meant to be exemplary only and that various materials and components are contemplated to be within the scope of the present invention. In the exemplary embodiment of FIG. 1, patient interface device 100 includes cushion assembly including a support cushion assembly 112 having a wedge 126, low durometer sealing member 119, and faceplate 116 which is coupled to a front portion of support cushion assembly 112. However, in another exemplary embodiment, patient interface device 100 includes a cushion assembly including a support cushion assembly having no wedge.

An opening 117 in faceplate 116 couples elbow conduit 110 to faceplate 116, thereby allowing breathing gas from pressure generating device 104 to be delivered to an interior space defined by support cushion assembly 112 and low durometer sealing member 119, and then to the patient's airway. Opening 117 also allows exhalation gas, such as gas exhaled by the patient, to be communicated to exhaust vent 113 located in elbow conduit 110.

Figure 5:
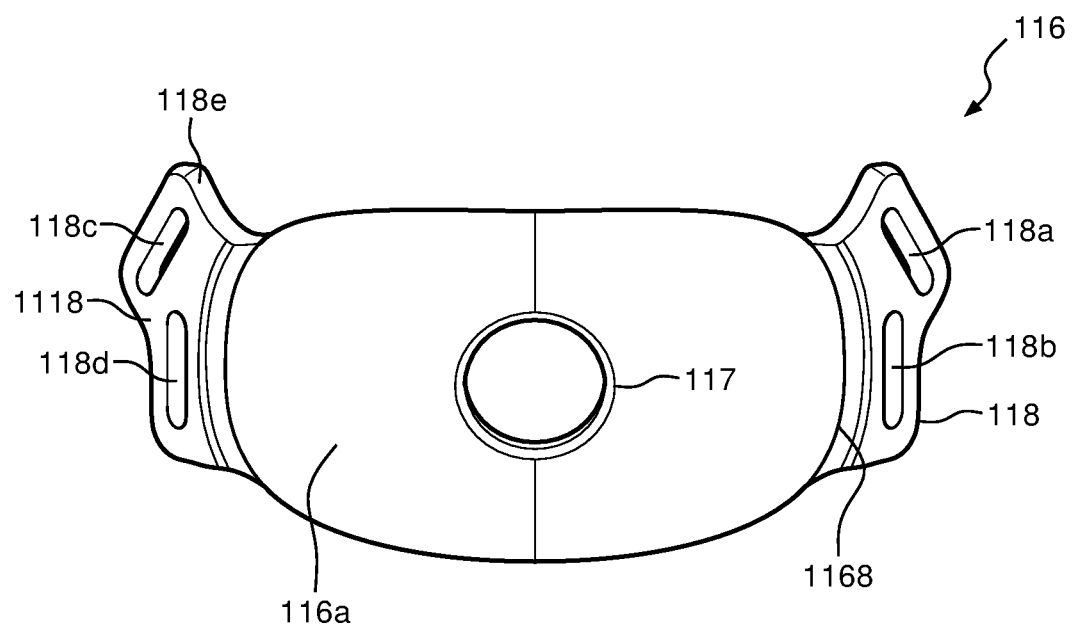
FIG. 5 is a front view of a faceplate for the patient interface device of FIG. 1 in accordance with various embodiments.

FIG. 5 is a front view of faceplate 116 for patient interface device 100 in accordance with various embodiments. In one exemplary embodiment, faceplate 116 is made of a low weight, thermoform material. For example, faceplate 116 may be made of a dense foam sandwiched between two pieces of polyester, or another type of fabric. As shown in FIG. 5, faceplate 116 has a headgear attachment area 118 and 1118, which are located at either end of the fabric faceplate, each being attached via a hinge 1168. Headgear straps may be attached to faceplate 116 using attachment members 118a and 118b, located within headgear attachment area 118, and attachment members 118c and 118d located within headgear attachment area 1118. For example, attachment members 118a and 118b are located on a first side of fabric faceplate 116 while attachment members 118c and 118d are located on a second side of fabric faceplate 116. Persons of ordinary skill in the art will recognize that any number of attachment members may be included, and the use of four attachment members 118a-d is merely exemplary.

Hinge 1168 is a portion of faceplate 116 that connects a main portion of faceplate 116 to headgear attachment areas 118 and 1118. Faceplate 116 includes a front portion 116a and a back portion 116b that are laminated together with a piece of high density foam in between. Front portion 116a and back portion 116 of faceplate 116 are made of a fabric, such as polyester, however they may also be customizable and therefore can be made of any other suitable material, and may have any suitable shape or configuration. In the illustrated embodiment, hinge 1168 does not include a foam piece therein, and therefore is more easily malleable about the patient's face to act as a hinge.

Headgear attachment areas 118 and 1118, however, are constructed similarly to the main portion of faceplate 116 in that a piece of high density foam is laminated between the two pieces of fabric. In some embodiments, however, hinge 1168 may include a piece of foam or any other material, or faceplate 116 may be continuous in structure throughout such that no hinge is present and faceplate 116 naturally contours about the patient's face. By making the faceplate out of a thermoform material instead of a substantially rigid material, a higher quality overall fit for the patient is achieved because faceplate 116 is more capable of conforming to the shape of the patient's face. A rigid faceplate, such as one made out of a hard plastic or metal, will not allow much, if any, contouring about the patient's face, thus leading to an uncomfortable wearing experience and poor seal.

Attachment areas 118 and 1118 are located on either side of the main portion of faceplate 116. Each attachment area 118 and 1118 includes two attachment members, with one member located on a protruding piece 118e. The protruding piece 118e enables the headgear straps to couple around a top of a patient's head via attachment members 118a and 118c, while attachment members 118b and 118d allow the headgear straps to couple around the back portion of the patient's head. These two separate sets of attachments members, 118a and 118c, and 118b and 118d, allow for the vertical and horizontal securing forces maintaining patient interface device 100 on the patient's face.

In some embodiments, faceplate 116 may be customizable. For example, the patient may select which fabric is going to be used for the faceplate and/or a color, texture, and/or pattern of the faceplate. As another example, the faceplate can be designed to fit the patient's face.

Figure 6:
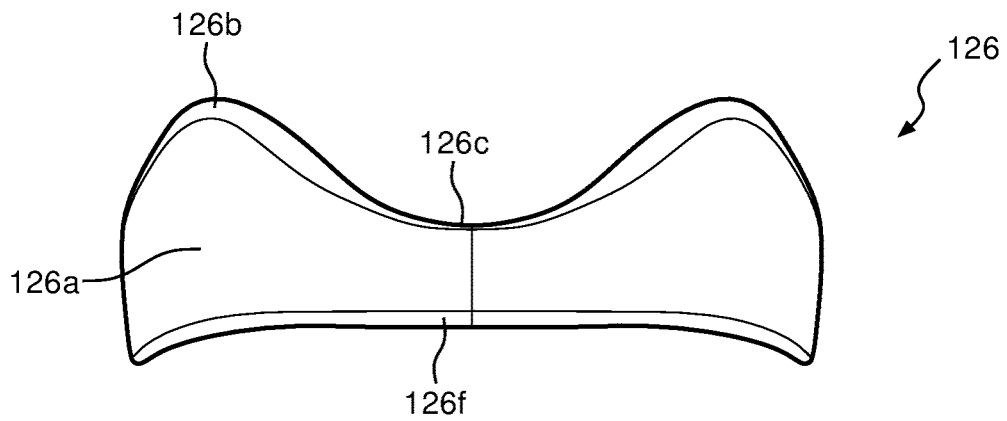
FIGS. 6-8 are front, top plane, and back views, respectively, of a wedge for a support cushion assembly of the minimal weight face mask of FIG. 1 in accordance with various embodiments.
Figure 7:
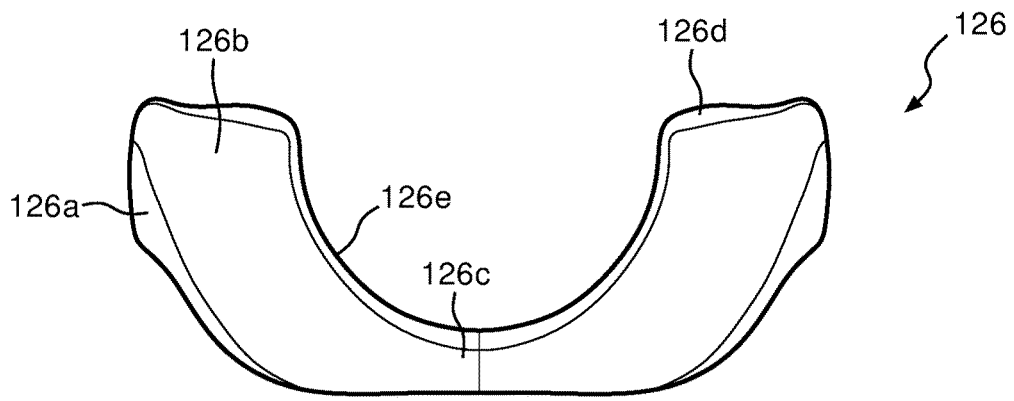
Figure 8:
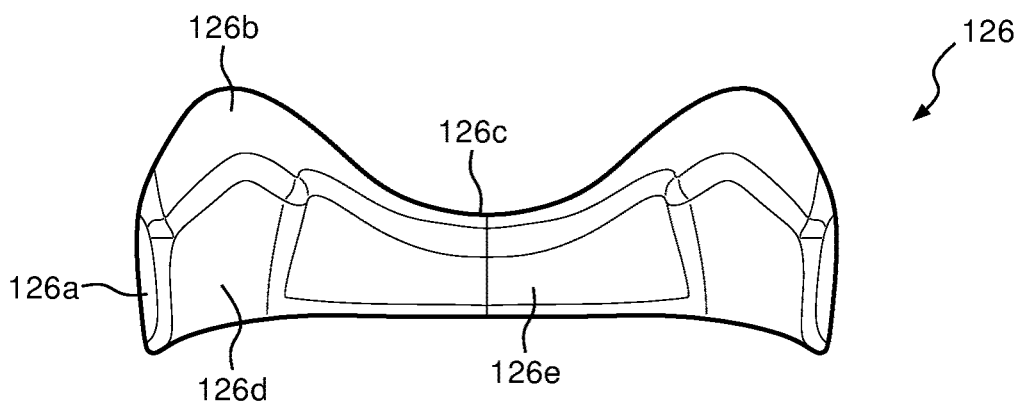

FIGS. 6-8 are front, top plane, and back views, respectively, of wedge 126 used with support cushion assembly 112 of patient interface device 100 in accordance with various embodiments. In one exemplary embodiment, wedge 126 is substantially "V"-shaped with an upper portion 126b making the upper portion of the V-shape, and a nasal resting portion 126c being the lower portion of the V-shape. Wedge 126 is oriented such that, when inserted into support cushion assembly 112, front portion 126a faces away from the patient, while an inner rear portion 126d and an outer rear portion 126e face toward the patient (within support cushion assembly 112). In the exemplary embodiments, wedge 126 contours about nasal resting portion 126c such that wedge 126 has a substantially curved design. Outer rear portion 126e further allows for a nasal orifice portion 112d to be formed within support cushion assembly 112.

In the exemplary embodiment, wedge 126 is formed out of a high density foam material, such as a 5 lbs. foam. However, persons of ordinary skill in the art will recognize that wedge 126 may be made out of other materials, including, but not limited to, gels, fabrics, silicone, cardboard, cork, etc. It can be appreciated that because wedge 126 is not disposed in the airway path, i.e., in contact with the air being communicated with the patient, it can be formed from materials that are otherwise not suited for use in the airway path, such as materials that are not biocompatible or tend to propagate bacterial growth. In one embodiment, wedge 126 is coupled to support cushion assembly 112 via a friction fit, however wedge 126 may be coupled to support cushion assembly 112 using any other suitable means so long as wedge 126 is capable of being removed.

Wedge 126 serves as a support for a patient's nose as the patient places their face, and in particular, their nasal region, about sealing member 119 and support cushion assembly 112. Wedge 126 will behave as a coil, wrapping around the patient's nose to provide support for patient interface device 100 while maintaining a light weight design. Furthermore, wedge 126 will also aid in reducing irritation points on the patient's face by helping to form a strong seal between the patient's face and sealing member 119. By wrapping around the patient's nose, wedge 126 allows for a substantially sealing fit to be formed between the patient's face and patient interface device 100. In one embodiment, the patient does not have to perform any additional adjustments because an accurate seal is formed by wedge 126 collapsing around the patient's nose.

Figure 9:
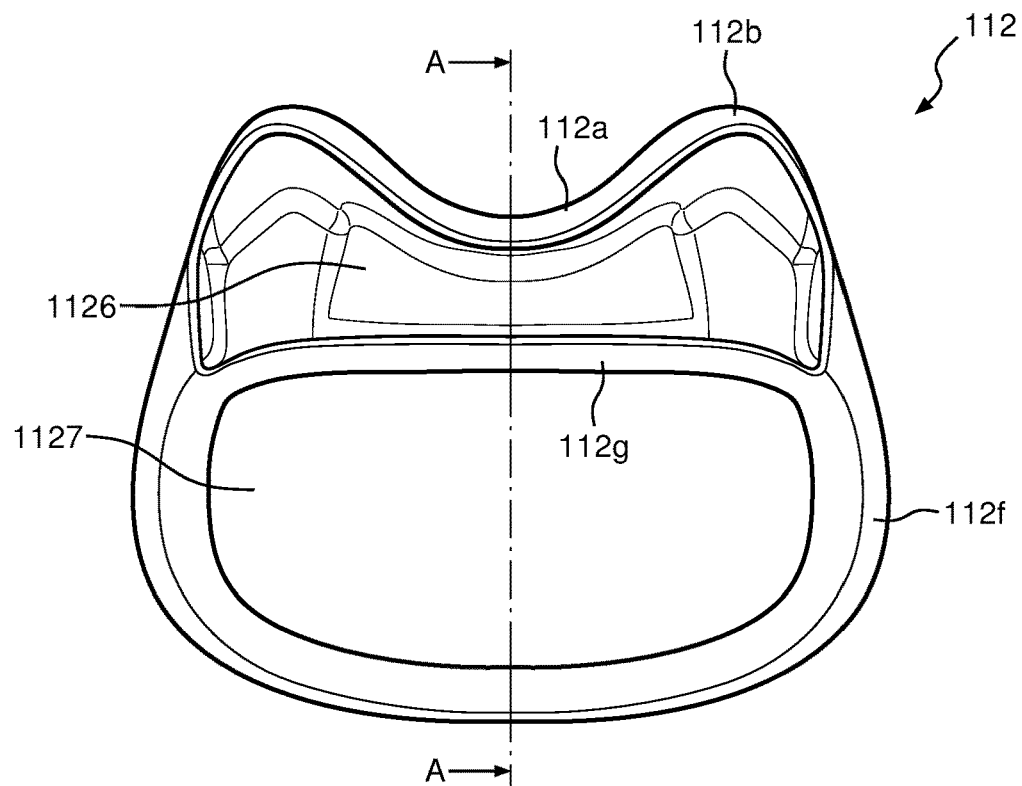
FIGS. 9 and 10 are a front view of the support cushion assembly for the patient interface device of FIG. 1 including a wedge receiving portion and without a wedge receiving portion, respectively, in accordance with various embodiments.
Figure 11:
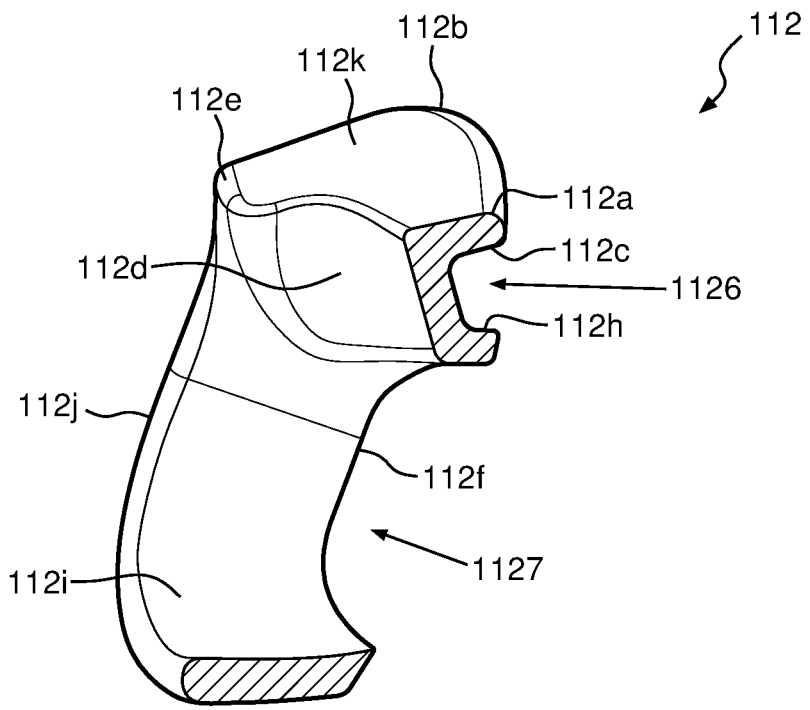
FIG. 11 is a cross-sectional view of the support cushion assembly taken along the lines A-A of FIG. 9, in accordance with various embodiments.

FIG. 9 is a front view of support cushion assembly 112 for patient interface device 100 of FIG. 1 without wedge 126 inserted therein in accordance with various embodiments. FIG. 11 is a cross-sectional view of cushion assembly 112 taken along the lines A-A of FIG. 9, in accordance with various embodiments. In one exemplary embodiment, support cushion assembly 112 includes an orifice 1127, which is capable of receiving sealing member 119. Orifice 1127 allows sealing member 119 to fit therein so that, when faceplate 116 is coupled to support cushion assembly 112, a patient's mouth may be located within the cavity formed by orifice 1127. Orifice 1127 is also sized such that sealing member 119 creates a substantially secure seal so that gases and air to be inhaled and also exhaled by the patient do not "leak" out from a faceplate interface portion 112g of support cushion assembly 112. Faceplate 116 is operable to abut faceplate interface portion 112g in one embodiment, however, in another embodiment, sealing member 119 fits over faceplate interface portion 112g such that faceplate 116 abuts sealing member 119 instead.

Support cushion assembly 112, of FIG. 9, is operable to receive wedge 126 within a wedge receiving portion 1126. Wedge receiving portion 1126, in one embodiment, resides above cushion orifice 1127, and includes an upper wedge receiving portion 112c and a lower wedge receiving portion 112h. When wedge 126 is placed into support cushion assembly 112 at wedge receiving portion 112b, upper portion 126b and nasal resting portion 126c of wedge 126 abut upper wedge receiving portion 112c, while a lower portion 126f of wedge 126 abuts lower wedge receiving portion 112h of support cushion assembly 112. The inner boundaries of orifice 112z are formed by an inner cushion orifice portion 112i, which, in one exemplary embodiment, is substantially circular.

In the exemplary embodiment, nasal orifice portion 112d (along with sealing member 119) creates a cavity that splints a patient's nostrils open and allows gas and air to be inhaled and/or exhaled. A patient's nose will rest above nasal resting portion 112a of support cushion assembly 112 such that the patient's nostrils reside substantially over nasal orifice portion 112d. A remaining portion of the user's face will abut sealing member 119, which is provided support by support cushion assembly 112 at various points. For example, face resting portion 112k, upper rear sealing portion 112e, and rear sealing portion 112j of support cushion assembly 112 will provide support for the patient's face interfacing with patient interface device 100 such that a suitable seal is formed between various portions of the patient's face (e.g., cheeks, cheekbones, mouth, chin, etc.) and patient interface device 100.

Sealing member 119 fits sealing over the front of support cushion assembly 112 at an upper portion 112b, nasal resting portion 112a, and a side sealing portion 112f. These are the portions of support cushion assembly 112 that point "away" from the patient's face. Sealing member 119, in the exemplary embodiment, fits sealing over the rear of cushion assembly 112 at upper rear sealing portion 112e, rear sealing portion 112j, and inner cushion orifice portion 112i. These are the portions of support cushion assembly 112 that point "towards" the patient's face. The cushion assembly, in one embodiment, is therefore formed by the inclusion of sealing member 119 onto support cushion assembly 112.

In one exemplary embodiment, support cushion assembly 112 is made of a lightweight foam material. For example, support cushion assembly 112 may be made out of a 3 lbs. foam. In the exemplary embodiment, support cushion assembly 112 is made out of a foam having a smaller density than the foam used to make wedge 126. However, persons of ordinary skill in the art will recognize that any type of foam, or any other material, such as a gel, fabric, or silicon, may be used to make support cushion assembly 112. In one embodiment, cushion assembly may be made of two or more foams each having a different density.

Figure 10:
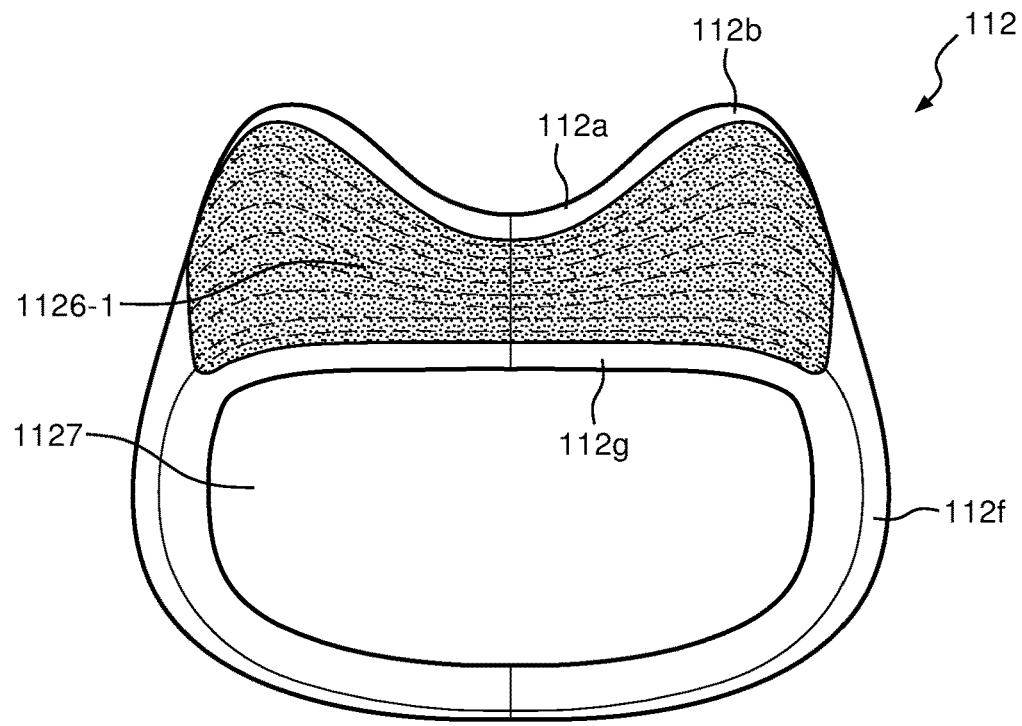

FIG. 10 is a front view of support cushion assembly 112 for patient interface device 100 of FIG. 1 not including a wedge receiving portion in accordance with various embodiments. In one exemplary embodiment, support cushion assembly 112 does not include a wedge, such as wedge 126. In this particular scenario, support cushion assembly 112 can be formed of a single material, such as foam, having multiple density values that vary for different sections of support cushion assembly 112. For example, in an area 112b-1 of support cushion assembly 112 where wedge 126 would be received, the foam is of a higher density than the foam making up the rest of support cushion assembly 112. In another embodiment, support cushion assembly 112 is made primarily of a first material, such as a low weight foam, whereas area 112b-1 of support cushion assembly 112 where wedge 126 would be received, is made of a different material, such as a gel.

Figure 12:
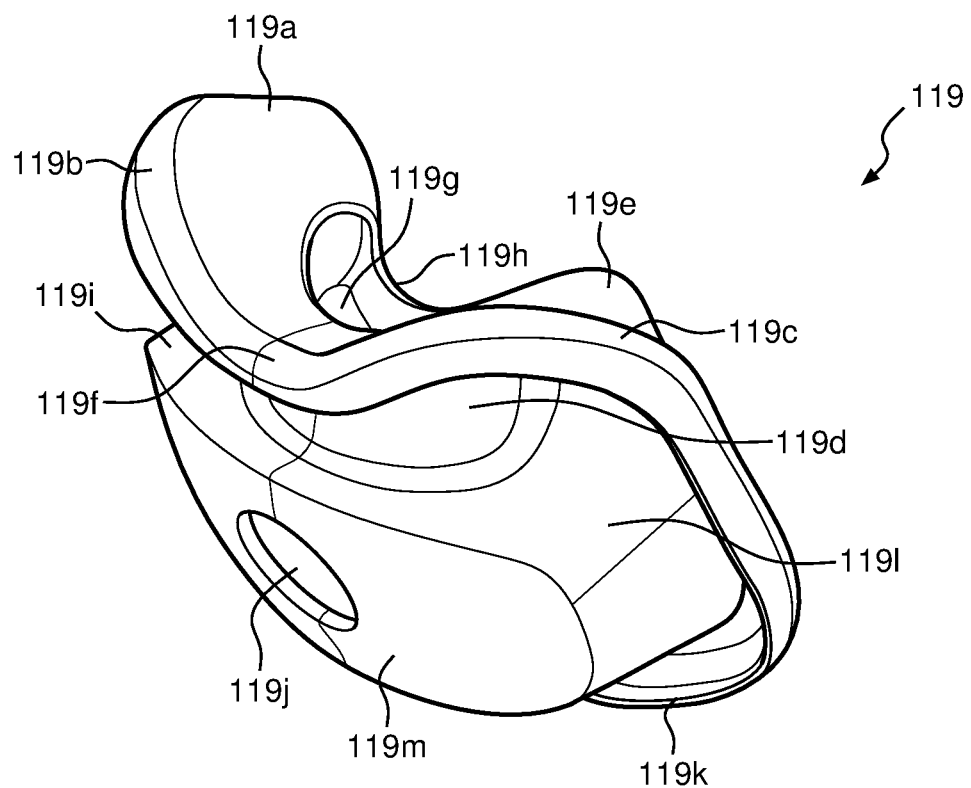
FIGS. 12 and 13 are isometric and front views of a sealing member for the patient interface device of FIG. 1 in accordance with an illustrated embodiment.
Figure 13:
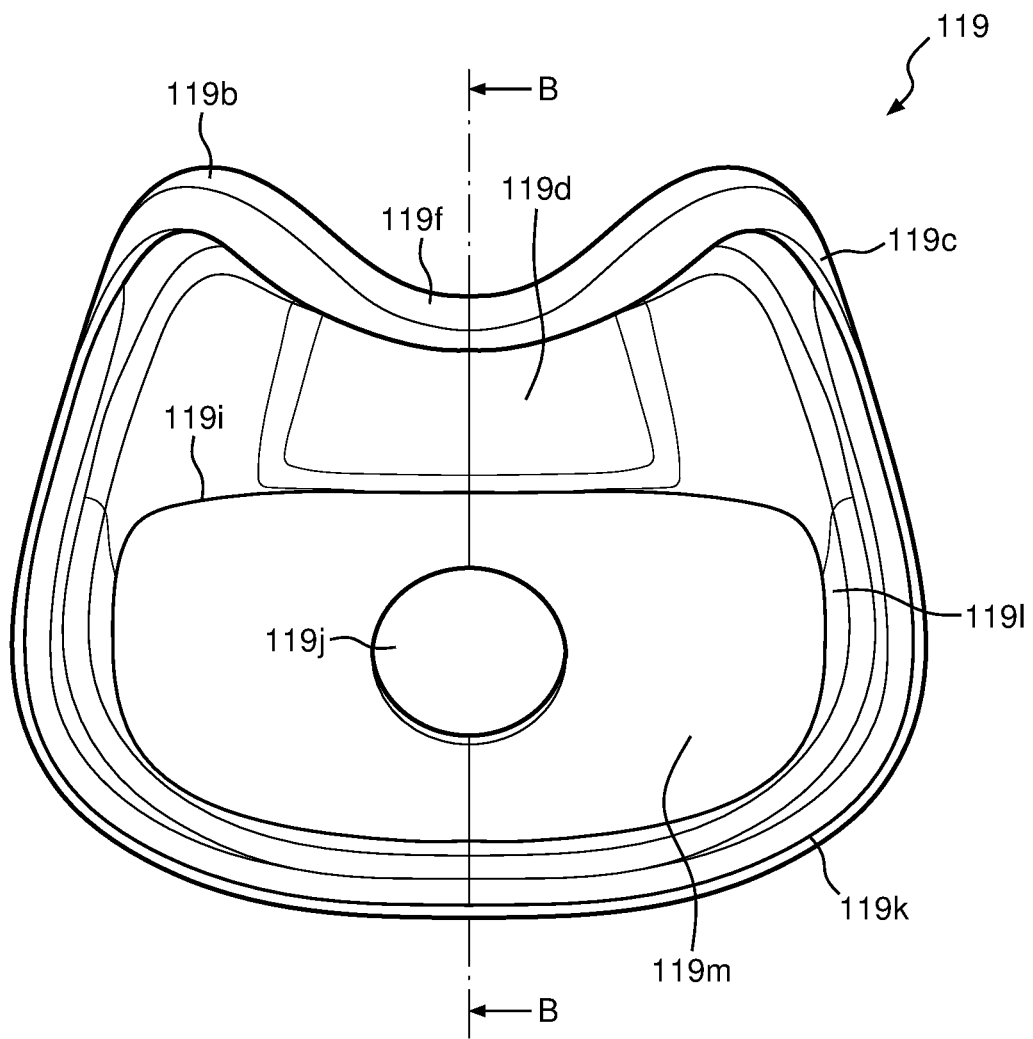
Figure 14:
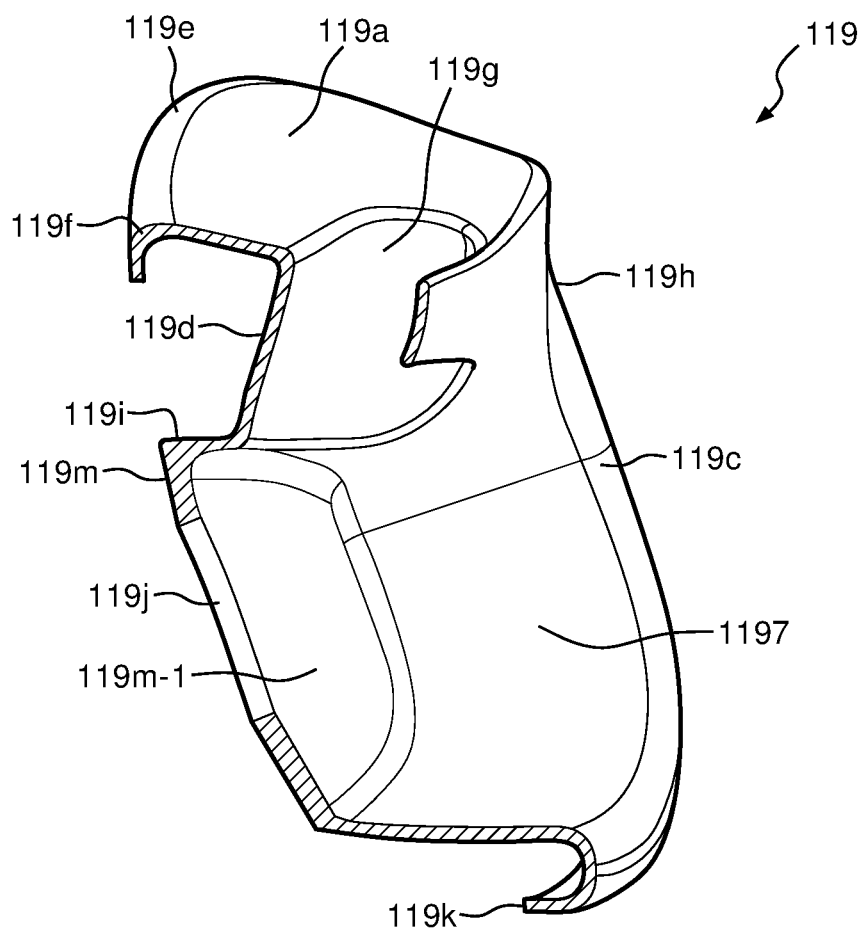
FIG. 14 is a cross-sectional view of the sealing member taken alone lines B-B of FIG. 13 in accordance with the illustrated exemplary embodiment.

FIGS. 12 and 13 are isometric and front views of sealing member 119 of patient interface device 100 in accordance with an illustrated embodiment, and FIG. 14 is a cross-sectional view of sealing member 119 of patient interface device 100 taken alone lines B-B of FIG. 13 in accordance with the illustrated embodiment. In one exemplary embodiment, sealing member 119 is made of silicon and has a low durometer. For example, sealing member 119 has a durometer of approximately 5-10 sH OO (±5%). Persons of ordinary skill in the art will recognize that although sealing member 119 is described being made of silicon and has a low durometer in the exemplary embodiment, other materials, such as gels or fabrics having other durometers, may be used instead. Sealing member 119 sealingly fits onto support cushion assembly 112, such that sealing member 119 abuts back portion 116b of faceplate 116. In the exemplary embodiment of FIG. 1, sealing member 119 fits over a majority of cushion assembly 112 (e.g., 50% or more), forming the cushion assembly, such that a patient's face interfaces only with sealing member 119. This allows for an accurate seal to be formed between the patient's face and patient interface device 100, while also enabling easy removal and cleaning of sealing member 119. The low durometer further provides a strong seal between the patient and patient interface device 100 as sealing member 119 is easily deformed about the various contours of the patient's face.

Sealing member 119 includes an opening 119j within a front faceplate portion 119m, which is operable to receive elbow conduit 110 through opening 117 in faceplate 116. Front faceplate portion 119m will, in the illustrated embodiment, directly abut faceplate 116 such that a seal is formed between faceplate 116 and sealing member 119. Front faceplate portion 119m extends outward, away from the patient's face, through orifice 112z. Residing above front faceplate portion 119m is a lower wedge portion 119i and a wedge portion 119d of sealing member 119. Front faceplate portion 119m and lower wedge portion 119i of sealing member 119 correspond to the areas of sealing member 119 that are in general contact with the areas of support cushion assembly 112 that receive wedge 126. Residing below front faceplate portion 119m is a front sealing portion 119k. Front sealing portion 119k is operable to receive rear sealing portion 112j of support cushion assembly 112 such that front sealing portion 119k abuts rear sealing portion 112j of support cushion assembly 112. Residing to the sides of front faceplate portion 119m is a side sealing portion 119l, which is operable to receive inner orifice portion 112i of support cushion assembly 112.

A side sealing portion 119c of sealing member 119 abuts side sealing portion 112f of support cushion assembly 112 such that an adequate seal is created at the sides of a patient's face. Furthermore, an upper sealing portion 119b and a front side sealing portion 119e interact with the patient's facial contours, forming a seal thereby, while also being supported by upper portion 112b and upper rear sealing portion 112e of support cushion assembly 112.

As a patient rests their face on patient interface device 100, the front of the patient's nose will reside on nasal resting portion 119f of sealing member 119, which is located above nasal resting portion 112a of support cushion assembly 112, which is further supported by wedge 126. Wedge 126 will collapse and allow nasal resting portion 119f and a nasal side shelf portion 119a to deform accordingly around the patient's nose, creating an accurate seal. For example, the patient may not have to perform any additional adjustments to patient interface device 100 because an accurate seal has been formed around the patient's nose (and face) by wedge 126 collapsing. The patient's nostrils, when contacting patient interface device 100, reside substantially over nasal orifice portion 119g, which is in fluid communication with nasal orifice portion 112d of support cushion assembly 112. Nasal orifice portion 119g of sealing member 119 allows the patient to inhale and exhale gas and/or air from pressure generating device 104 and/or from the patient themselves. Sealing member 119 further includes a nasal sealing flap portion 119h, which created a back wall of nasal orifice portion 119g of sealing member 119. Nasal sealing flap 119h of sealing member 119 will contact the patient's face just below the nose and just above the lip. Nasal sealing flap 119h of sealing member 119, in the illustrated embodiment, does not include any additional support from support cushion assembly 112, thereby allowing a maximum amount of deformity to exhaust between sealing member 119 and the patient. Furthermore, the low durometer of flap 119h of sealing member 119 allows the patient's face to compress and deform sealing member 119 such that seal is created between the patient's face and sealing member 119 of patient interface device 100.

As shown in FIG. 14, the patient will fluidly interact with sealing member 119 such that minimal contact is made directly between the patient's face and support cushion assembly 112. The patient's mouth area will generally be in contact about a rear faceplate portion 119m-1 and a sealing member orifice portion 119l of sealing member 119, both of which, together, form the front, sides, and bottom portions of the main cavity in patient interface device 100 that allows air and gas to be transmitted to and from elbow conduit 110 and the patient.

Figure 15:
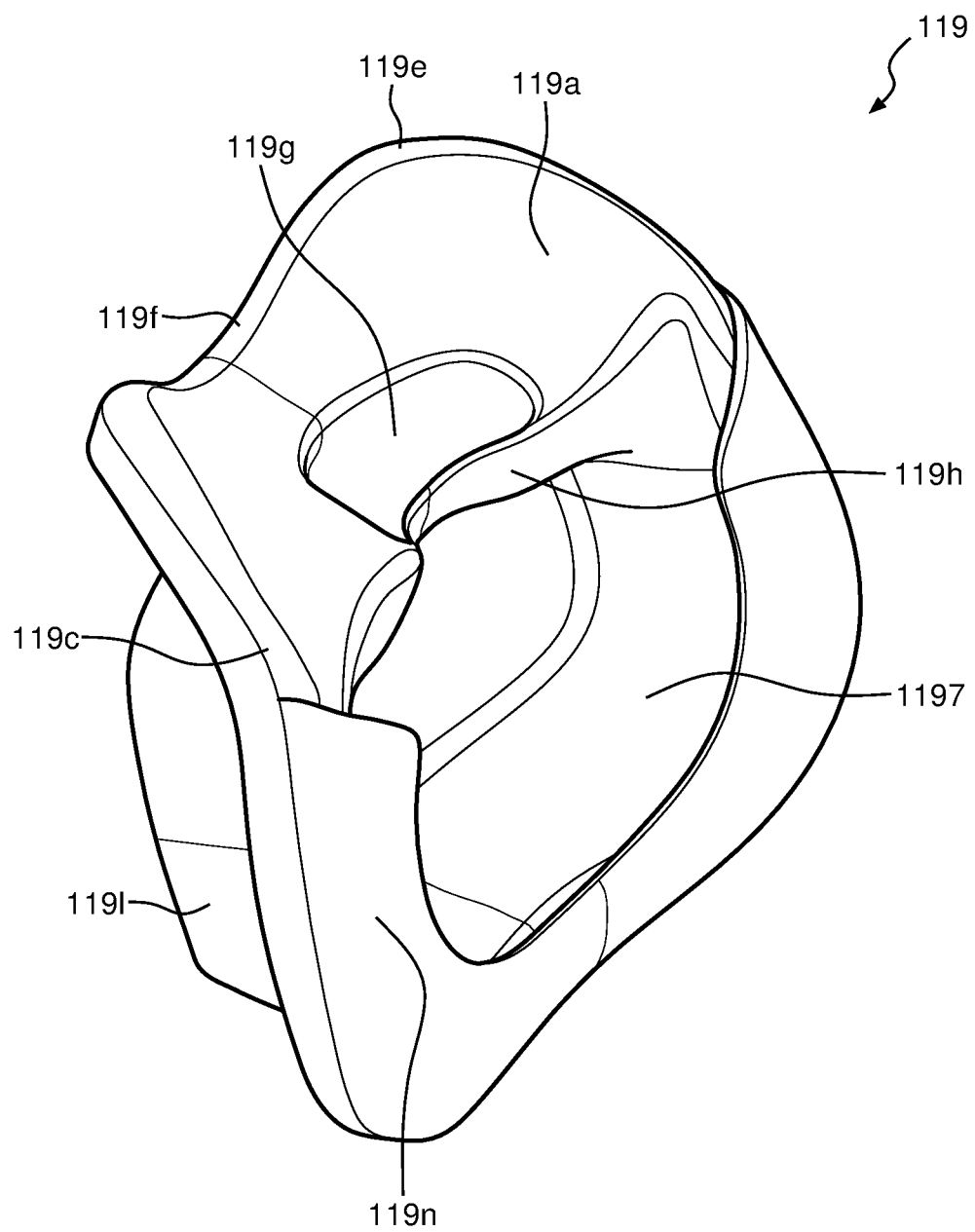
FIG. 15 is an isometric view of another sealing member for the patient interface device of FIG. 1 in accordance with an illustrated embodiment.

FIG. 15 is an isometric view of another sealing member for patient interface device 100 in accordance with an illustrated embodiment. In the illustrated exemplary embodiment, sealing member 119 includes a second flap 119n, that further provides a fluid seal between sealing member 119 of patient interface device 100 and the patient's face. Second flap 119 wraps around a lower portion of the rear of sealing member 119 and extends into sealing member orifice portion 119l slightly so that when a patient places his/her face on patient interface device 100, second flap 119 deforms into sealing member orifice portion 119l. Second flap 119, in one embodiment, can be thought of as an extra piece of material that further extends the edge of sealing member 119 so that more surface area of sealing member 119 can interact with the patient's face, thereby increasing the quality of the seal formed between the patient's face and patient interface device 100. Persons of ordinary skill in the art will recognize that any amount of extra material may be used to form second flap 119n, and second flap 119n may have any suitable shape.

Figure 16:
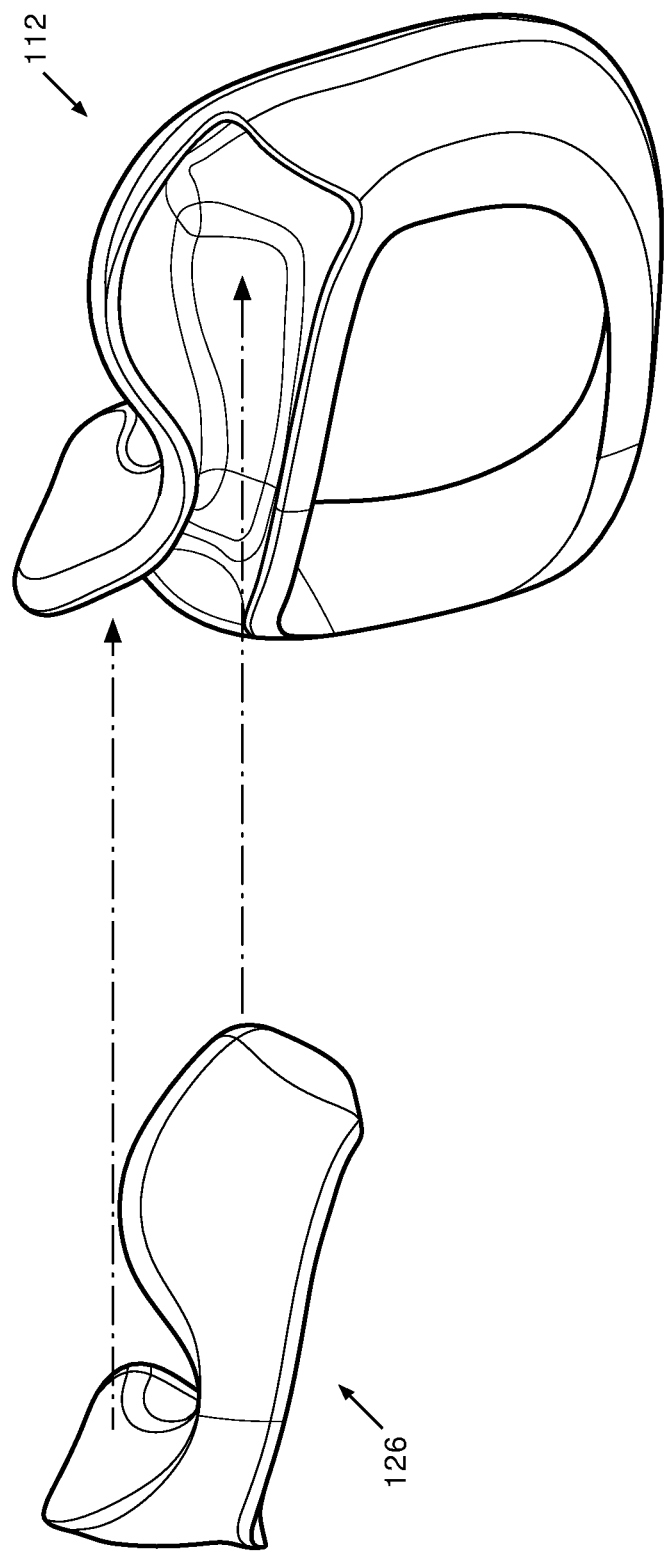
FIG. 16 is a schematic illustration of how a wedge is received by a support cushion assembly in accordance with various embodiments.

FIG. 16 is a schematic illustration of how wedge 126 couples to support cushion assembly 112 of patient interface device 100 in accordance with various embodiments. In the illustrated exemplary embodiment, wedge 126 is a one-directional fit component that friction fits into support cushion assembly 112 within wedge receiving portion 112b of support cushion assembly 112. Wedge 126 is substantially "V"-shaped, and fits within the horseshoe-shaped recess of receiving portion 112b. Although wedge 126 fits into support cushion assembly 112 via a friction fit (e.g., akin to a puzzle piece), wedge 126 is also removable from support cushion assembly 112. In other embodiments, wedge 126 may snap fit, Velcro-fit, pressure fit, or use any other type of fixing means to secure it within support cushion assembly 112. In one embodiment, wedge 126 is not removable from support cushion assembly 112, and may, for example, be glued or permanently secured within support cushion assembly 112.

Figure 17:
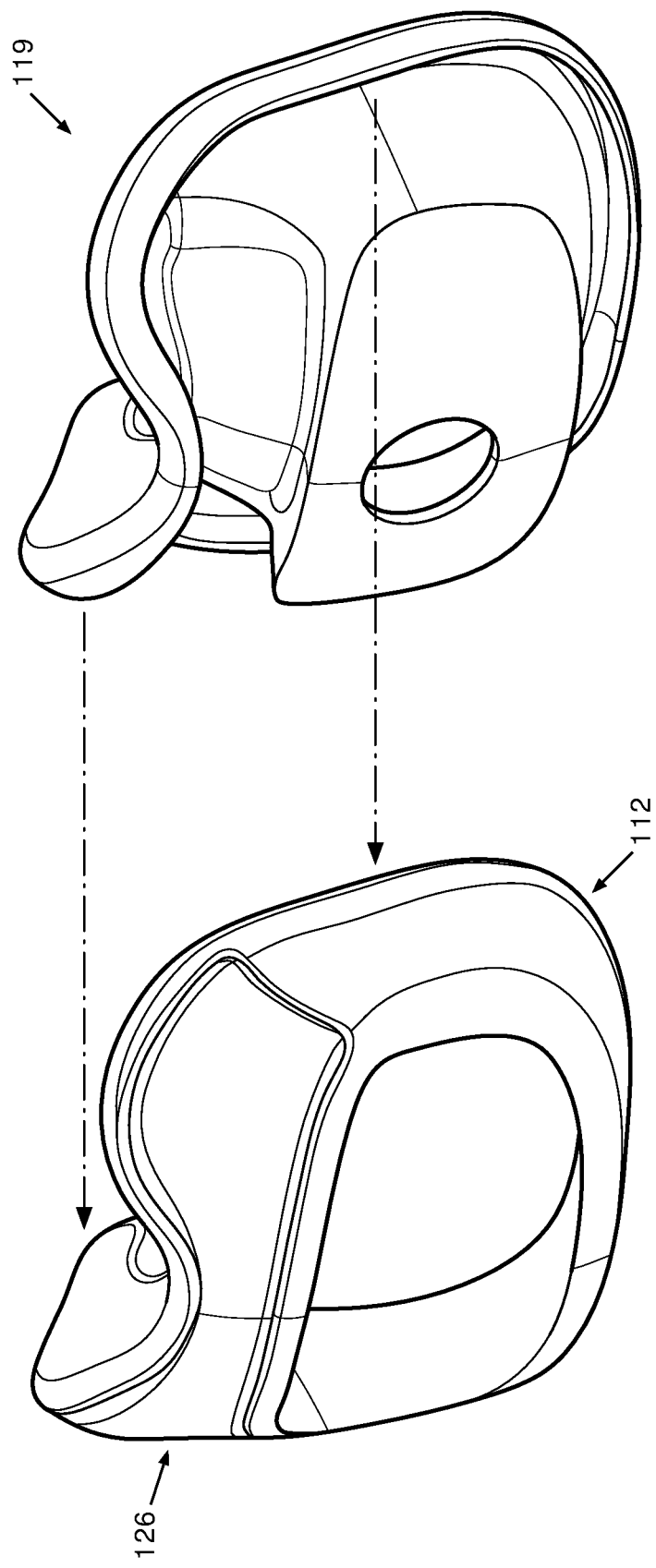
FIG. 17 is a schematic illustration of how a sealing member couples to the support cushion assembly including the wedge of FIG. 16 in accordance with various embodiments.

FIG. 17 is a schematic illustration of how sealing member 119 couples to cushion assembly 112 including wedge 126 in accordance with various embodiments. In the illustrated embodiment, sealing member 119 is placed onto support cushion assembly 112 from the back of support cushion assembly 112, such that sealing member 119 fits over nasal resting portion 112a, upper portion 112b, face resting portion 112k, upper rear sealing portion 112e, rear sealing portion 112j, inner cushion orifice portion 112i, and side sealing portion 112f. Sealing member 119 will also fit through orifice 112l such that front portion 119m of sealing member 119 will abut back portion 116b of faceplate 116. In the illustrated embodiment, sealing member 119 does not fit over wedge 126, however persons of ordinary skill in the art will recognize that this is merely exemplary and in other embodiments, sealing member 119 will fit over front portion 126a of wedge 126. Sealing member 119 is designed such that only minimal portions of patient interface device 100 not including sealing member 119 contact the patient's face. In the illustrated embodiment, sealing member 119 fits over some or all of support cushion assembly 112 and is secured thereon by means of a friction fit, however other securing means are also possible including, but not limited to, Velcro, glue, snaps, straps, or any other securing means, or any combination thereof. The cushion assembly is therefore formed by sealing member 119 being fit onto support cushion assembly 112.

Figure 18:
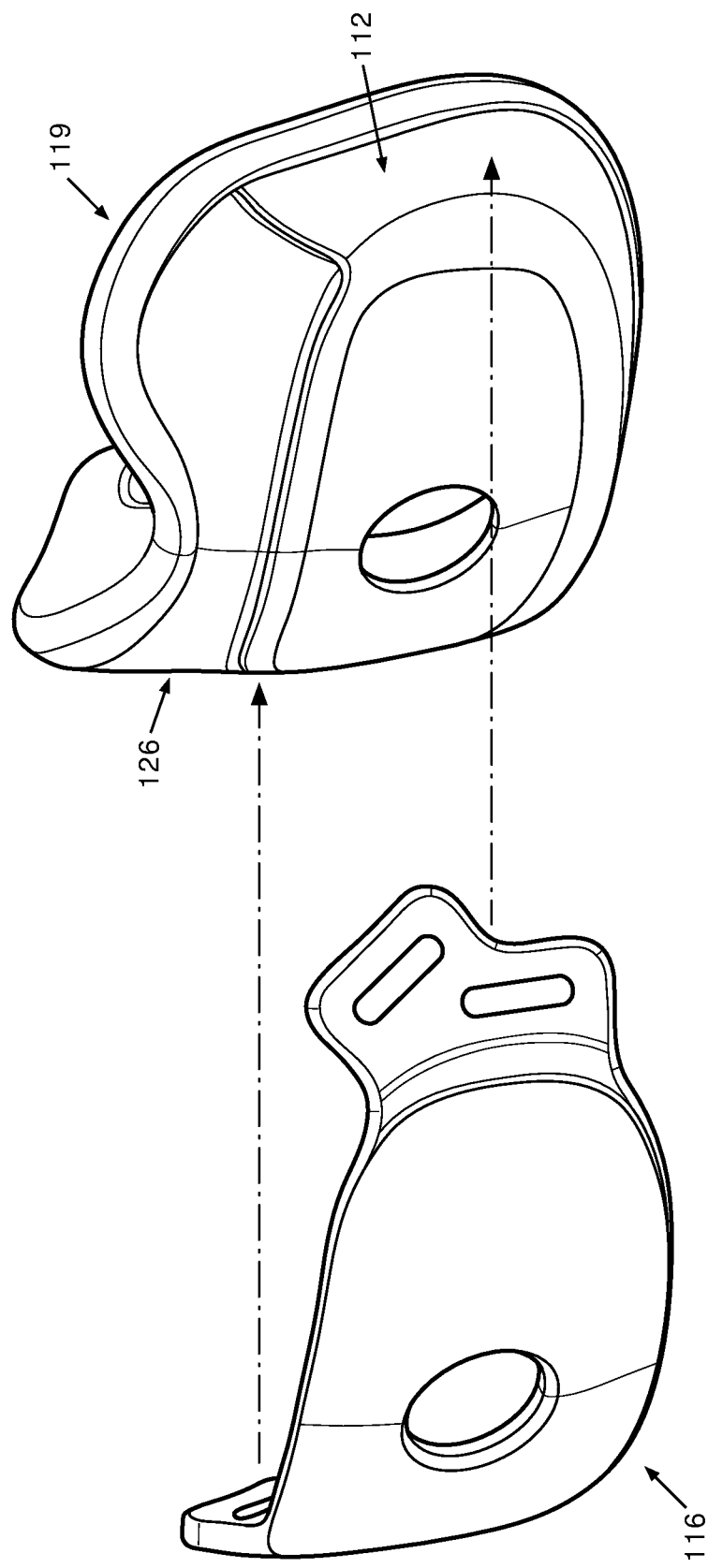
FIG. 18 is a schematic illustration of how a faceplate couples to a cushion assembly including the wedge and the sealing member of FIG. 17 in accordance with various embodiments.

FIG. 18 is a schematic illustration of how faceplate 116 couples to the cushion assembly including support cushion assembly 112 including wedge 126 and sealing member 119 in accordance with various embodiments. In the illustrated embodiment, after sealing member 119 is placed over the cushion assembly including support cushion assembly 112 including wedge 126, faceplate 116 is attached to the front of the cushion assembly including support cushion assembly 112 and sealing member 119. Back portion 116b of faceplate 116 will abut front portion 119m of sealing member 119. In one exemplary embodiment, back portion 116b of sealing member 116 will also reside in front of lower wedge receiving portion 112h and a portion or all of front portion 126a of wedge 126. In one embodiment, faceplate 116 is affixed to support cushion assembly 112 and/or sealing member 119 using a friction fit, however persons of ordinary skill in the art will recognize that any other suitable means may be used to secure faceplate 116 to patient interface device 100 including, but not limited to, Velcro, straps, snaps, or any other securing means, or any combination thereof. In one embodiment, faceplate 116 does not secure to patient interface device 100, and merely resides thereon with headgear coupled to attachment members 118a-d providing a force on faceplate 116 that maintains faceplate 116 to patient interface device 100.

It can be appreciated that the present invention provides a generally low weight face mask that minimizes patient discomfort while maintaining a quality seal between the patient and the mask, thereby making the administration of the breathing therapy less burdensome for the patient.

Figure 19:
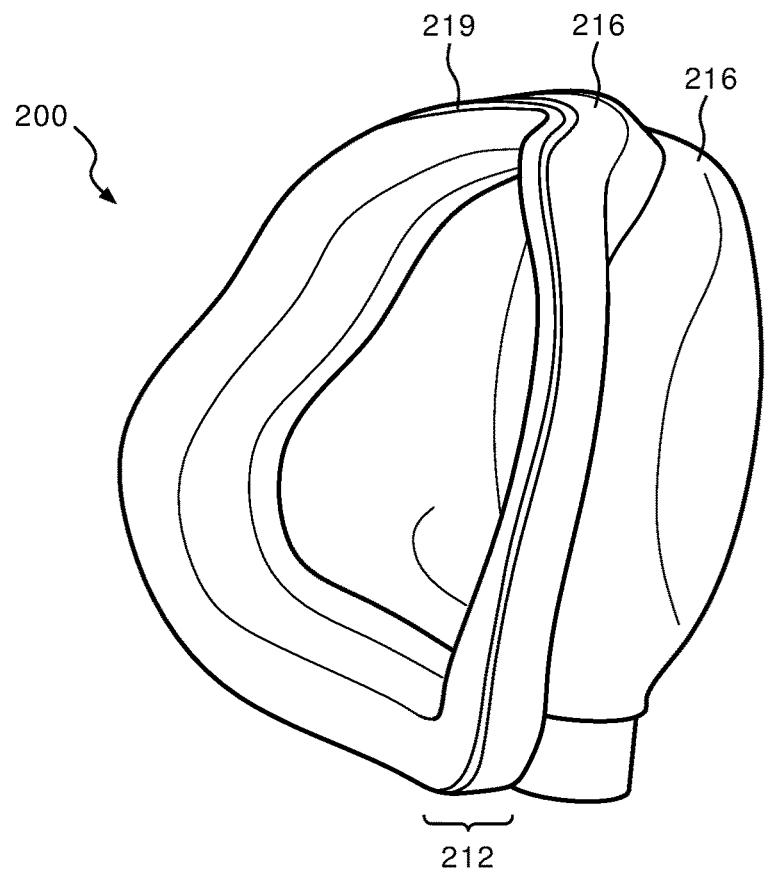
FIG. 19 is an isometric view of a further embodiment of patient interface device according to the principles of the present invention.
Figure 20:
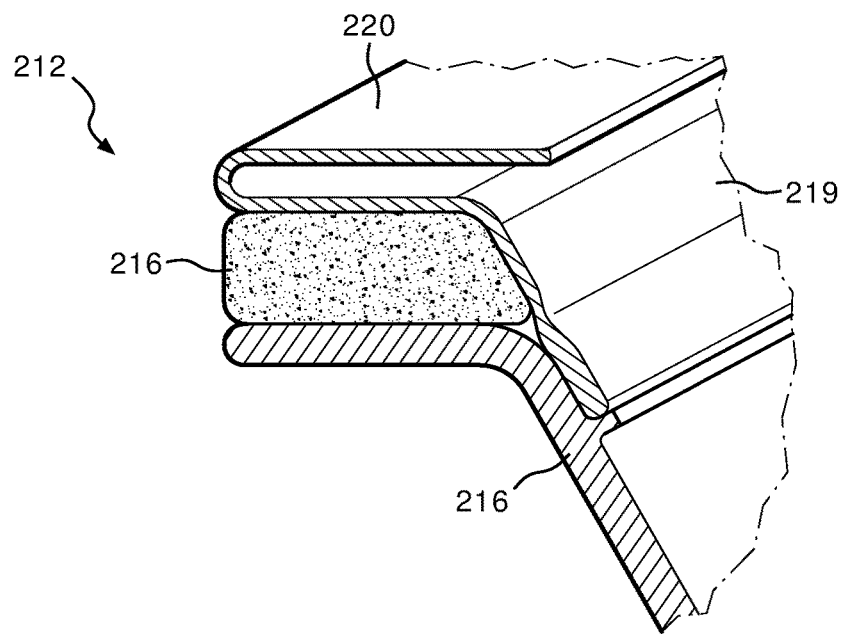
FIG. 20 is a sectional view of a cushion assembly in the patient interface device of FIG. 19.

FIG. 19 is an isometric view of a further embodiment of patient interface device 200 according to the principles of the present invention, and FIG. 20 is a sectional view of a cushion assembly 212 in patient interface device 200. Patient interface device includes a faceplate or shell 216 and a cushion assembly 212 operatively coupled to the shell in any suitable manner. Cushion assembly 202 includes a support cushion 226 and a sealing member 219 having a patient sealing portion 220.

In the illustrated embodiment, support cushion 226 is disposed around the perimeter of the shell between a flap formed by a portion of the shell and sealing portion 220 of sealing member 219. It can be appreciated, however, that support cushion 226 can be provided only in selective locations between the sealing flap and the rest of the patient interface.

In the exemplary embodiment, support cushion 226 is formed out of a high density foam material, such as a 5 lbs. foam. However, persons of ordinary skill in the art will recognize that support cushion 226 may be made out of other materials, including, but not limited to, gels, fabrics, silicone, cardboard, cork, etc. It can be further appreciated that because support cushion 226 is not disposed in the airway path, i.e., in contact with the air being communicated with the patient, it can be formed from materials that are otherwise not suited for use in the airway path, such as materials that are not biocompatible or tend to propagate bacterial growth.

In an exemplary embodiment, sealing member 219, like sealing member 119, is made of silicon and has a low durometer. For example, sealing member 219 has a durometer of approximately 5-10 sH OO (±5%). Persons of ordinary skill in the art will recognize that although sealing member 219 is described being made of silicon and has a low durometer in the exemplary embodiment, other materials, such as gels or fabrics having other durometers, may be used instead. Sealing member 219 sealingly fits onto the support cushion assembly such that the sealing member abuts a portion of the faceplate. In this embodiment, the sealing member and the faceplate together define the walls of the patient receiving orifice. Of course, the sealing member can be configured such that it alone defines the walls of the patient receiving orifice.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device operable to deliver a flow of breathing gas to a user, the device comprising:
    a cushion assembly, the cushion assembly comprising:
        a support cushion assembly defining a first orifice extending through the support cushion assembly, the support cushion assembly having at least one wall defining an inner surface of the support cushion assembly; and
        a sealing member disposed in the first orifice and covering the inner surface defined by the at least one wall, wherein the sealing member defines a patient receiving orifice for receiving a portion of a face of the user responsive to the patient interface device being donned by the user; and wherein the sealing member provides a sealing surface for creating a seal against the face of the user responsive to the patient interface device being donned by the user and prevents the support cushion assembly from contacting the face of the user, and wherein the support cushion assembly and the sealing member are not elements of a unitary body;
    a wedge, wherein the support cushion assembly further comprises a wedge receiving portion that is operable to receive the wedge; and
    a faceplate comprising a back portion that is placed over a front faceplate portion of the sealing member such that the faceplate abuts the sealing member and at least a portion the support cushion assembly, wherein the portion of the support cushion assembly that the faceplate abuts is proximate the wedge and the wedge receiving portion;
    wherein the wedge is made of a first material, the support cushion assembly is made of a second material, the sealing member is made of a third material, and the faceplate is made of a fourth material, and wherein the first material comprises a first density foam, the second material comprises a second density foam, the third material comprises silicone, and the fourth material comprises a thermoform material.

2. The patient interface device of claim 1, wherein the first density foam comprises a 5 lbs. foam; and the second density foam comprises a 3 lbs. foam.

3. The patient interface device of claim 1, wherein the thermoform material comprises a third density foam laminated between a first piece of fabric and a second piece of fabric, and the third density foam has a higher density than the first density foam and the second density foam.

4. The patient interface device of claim 1, wherein the sealing member has a durometer value that is approximately 5-10 Shore 00.

5. The patient interface device of claim 1, wherein the wedge comprises: support cushion assembly further comprises:
    a wedge comprising:
        an upper portion and a nasal resting portion that both interface with an upper wedge receiving portion of the support cushion assembly when the wedge is received by the support cushion assembly; and
        an inner rear portion and an outer rear portion, which interface with the wedge receiving portion when the wedge is received by the support cushion assembly.

6. The patient interface device of claim 1, wherein the support cushion assembly comprises a wedge, wherein the wedge is coupled to the support cushion assembly via a friction fit.

7. The patient interface device of claim 1, wherein the support cushion assembly further comprises a wedge that is deformable about the user's nose when the user rests the user's nose on a nasal resting portion of the sealing member; and has a generally "V"-shaped design when viewed from a front perspective and a substantially horseshoe-shaped design when viewed from a top perspective.

8. The patient interface device of claim 1, wherein the sealing member further comprises a second flap that extends from an edge of the sealing member towards the patient receiving orifice such that, when donned by the user, the second flap deforms around a portion of the user's face to increase a quality of the seal created between the user's face and the sealing member.

9. The patient interface device of claim 1, wherein the sealing member is operable to fit over the support cushion assembly from behind such that a front faceplate portion of the sealing member protrudes through the first orifice.

10. The patient interface device of claim 1, wherein the faceplate comprises: further comprising,
   a faceplate comprising:
      a back portion that is placed over a front faceplate portion of the sealing member such that the faceplate abuts the sealing member and at least a portion the support cushion assembly; and
      a faceplate opening therein that is in fluid communication with an elbow conduit to provide gas to the user.

11. The patient interface device of claim 10, wherein the sealing member further comprises a sealing member opening that is in fluid communication with a faceplate opening of a fabric faceplate such that gas provided to the user flows from the elbow conduit through the faceplate opening and the sealing member opening into the patient receiving orifice.

12. The patent interface device of claim 1, wherein the sealing member further comprises a flap portion that is operable to contact a region of the user's face below the user's nose and above the user's lips.

13. The patient interface device of claim 12, wherein the flap portion of the sealing member forms a back end of a nasal orifice portion of the sealing member, and wherein the nasal orifice portion is operable to allow the user's nostrils to be in fluid communication with the patient receiving orifice.

14. The patient interface device of claim 1, wherein the faceplate comprises further comprising:
   a faceplate comprising:
      a back portion that is placed over a front faceplate portion of the sealing member such that the faceplate abuts the sealing member and at least a portion of the support cushion assembly; and
      a first and a second headgear attachment area that are located at either side of the faceplate such that when the user wears the patient interface device, the first and second headgear attachment areas are located on a right and left side of the user's face.

15. The patient interface device of claim 14, wherein:
the first headgear attachment area comprises two attachment members located on a left side of the faceplate corresponding to the left side of the user's face, and two attachment members located on a right side of the faceplate corresponding to the right side of the user's face; and
each attachment member receives a portion of a headgear strap operable to secure the patient interface device to the user while in use.

* * * * *